United States Patent
Shiflett et al.

(10) Patent No.: US 8,771,626 B2
(45) Date of Patent: Jul. 8, 2014

(54) PROCESS FOR PURIFYING PERFLUORINATED PRODUCTS

(75) Inventors: Mark Brandon Shiflett, New Castle, DE (US); Akimichi Yokozeki, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 868 days.

(21) Appl. No.: 11/755,367

(22) Filed: May 30, 2007

(65) Prior Publication Data

US 2007/0297965 A1     Dec. 27, 2007

Related U.S. Application Data

(60) Provisional application No. 60/809,663, filed on May 31, 2006.

(51) Int. Cl.

| C01B 21/06  | (2006.01) |
|---|---|
| C01B 21/088 | (2006.01) |
| C01B 7/00   | (2006.01) |
| C01B 9/08   | (2006.01) |
| B01D 53/56  | (2006.01) |
| B01D 53/86  | (2006.01) |
| C01B 21/00  | (2006.01) |
| B01D 53/50  | (2006.01) |
| B01D 53/68  | (2006.01) |
| B01D 53/70  | (2006.01) |

(52) U.S. Cl.
USPC .......... 423/406; 423/383; 423/462; 423/489; 423/235; 423/240 R

(58) Field of Classification Search
USPC .................................................. 423/406, 400
See application file for complete search history.

(56) References Cited

U.S. PATENT DOCUMENTS

| 5,340,555 | A  | * | 8/1994  | Mashio et al. .......... 423/240 R |
|---|---|---|---|---|
| 5,827,602 | A  | * | 10/1998 | Koch et al. ................. 429/328 |
| 6,458,249 | B2 | * | 10/2002 | Miller et al. ................ 203/51 |
| 6,579,343 | B2 |   | 6/2003  | Brennecke |
| 7,208,605 | B2 |   | 4/2007  | Davis |
| 7,314,962 | B2 |   | 1/2008  | Harmer |
| 7,964,760 | B2 |   | 6/2011  | Shiflett |
| 8,075,777 | B2 |   | 12/2011 | Shiflett |
| 8,313,558 | B2 |   | 11/2012 | Shiflett |
| 8,536,371 | B2 |   | 9/2013  | Davis |
| 2002/0001560 | A1 | * | 1/2002 | Miller et al. ................ 423/406 |
| 2004/0133058 | A1 | * | 7/2004 | Arlt et al. ................... 585/833 |
| 2006/0226072 | A1 | * | 10/2006 | Wyse et al. ................. 210/634 |

(Continued)

FOREIGN PATENT DOCUMENTS

WO    WO 2005/113702 A1    12/2005

OTHER PUBLICATIONS

Examining Purification and Certification Strategies for High-Purity C2F6 Process Gas, Micro Magazine, 1998, pp. 35-52.

(Continued)

Primary Examiner — Melvin C Mayes
Assistant Examiner — Michael Forrest

(57) ABSTRACT

This invention relates to a process for purifying at least one of perfluoromethane and nitrogen trifluoride from a mixture thereof using an ionic liquid. The process may be performed by a technique such as extractive distillation or absorption wherein at least one ionic liquid is used as the entraining agent or absorbent, respectively.

12 Claims, 1 Drawing Sheet

A schematic diagram of a simple extractive distillation system

(56) References Cited

U.S. PATENT DOCUMENTS

2006/0226074 A1* 10/2006 Wyse et al. .................. 210/634
2007/0131535 A1   6/2007 Shiflett
2010/0143994 A1   6/2010 Erdner-Tindall
2013/0123448 A1   5/2013 Noelke

OTHER PUBLICATIONS

Rogers et al., Ionic Liquids—Solvents of the Future, Science, 2003, vol. 302:792-793.
Kenneth R. Seddon, Ionic Liquids for Clean Technology, J. Chem. Tech. Biotechnol., 1997, vol. 68:351-356.
Olivier et al., Nonaqueous Room-Temperature Ionic Liquids: A New Class of Solvents for Catalytic Organic Reactions, Chem. Ind., 1996, vol. 68:249-263.
John E. Enderby, Ionic Liquids: Recent Progress and Remaining Problems, J. Phys. Condensed Matter., 1993, vol. 5:B99-B106.
Michael Freemantel, Designer Solvents, Ionic Liquids May Boost Clean Technology Development, Chemical and Engineering News, 1998, pp. 32-37.
Gordon et al., Ionic Liquid Crystals: Hexafluorophosphate Salts, J. Mater. Chem., 1998, vol. 8:2627-2636.
Thomas Welton, Room-Temperature Ionic Liquids. Solvents for Synthesis and Catalysis, Chem. Rev., 1999, vol. 99:2071-2084.
Edgar W. Slocum, Multipurpose High-Pressure Phase-Equillibrium Apparatus, Ind. Eng. Chem. Fundam., 1975, vol. 14:126.
William Schotte, Collection of Phase Equillibrium Data for Separation Technology, Ind. Eng. Chem. Process Des. Dev., 1980, vol. 19:432-439.
Shiflett et al., 2006, Solubility and Diffusivity of Hydrofluorocarbons in Room Temperature Ionic Liquids, vol. 52:1205-1219.

* cited by examiner

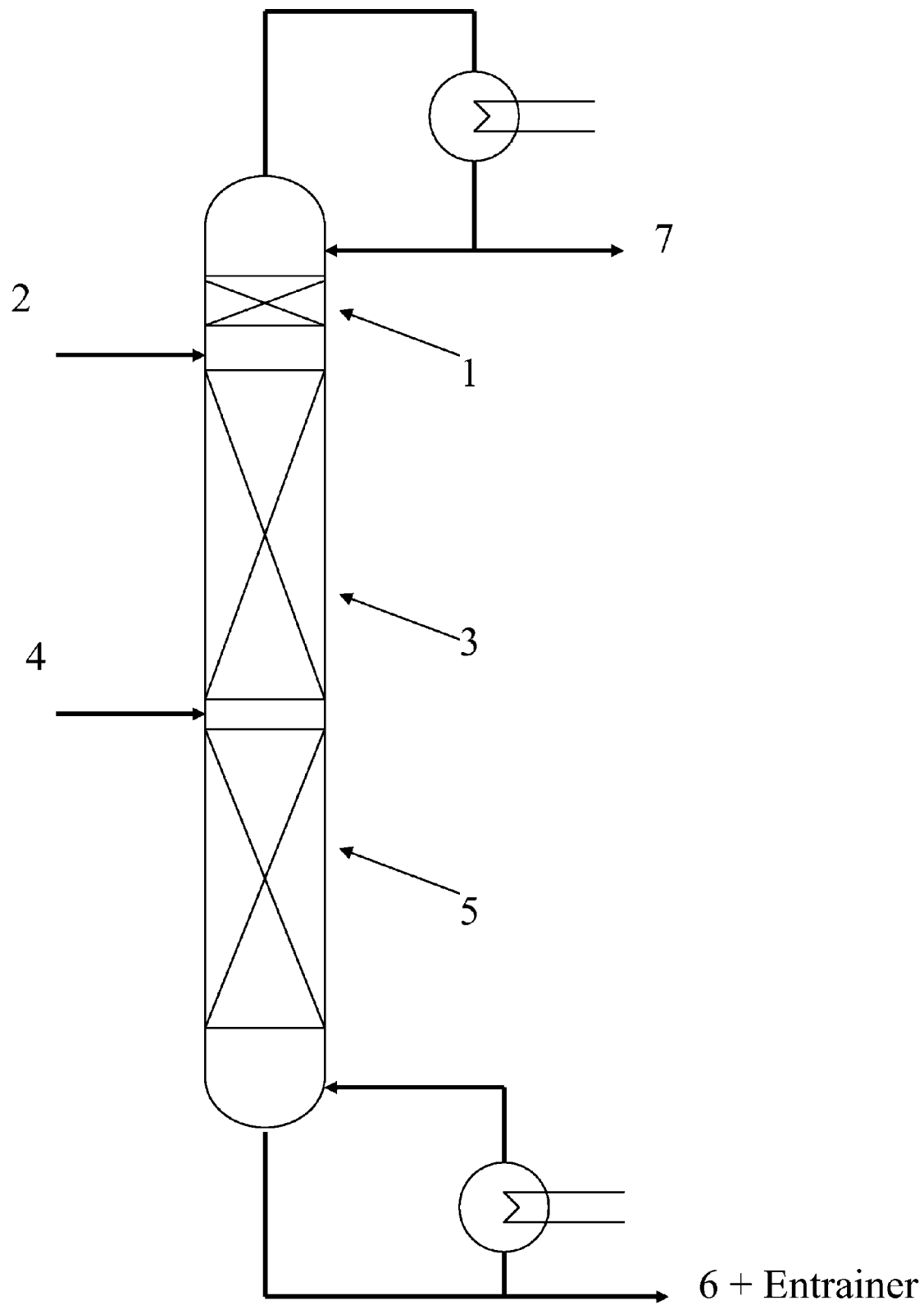
A schematic diagram of a simple extractive distillation system

PROCESS FOR PURIFYING PERFLUORINATED PRODUCTS

This application claims the benefit of U.S. Provisional Application No. 60/809,663, file May 31, 2006, which is incorporated in its entirety as a part hereof for all purposes.

TECHNICAL FIELD

The present invention relates to a process for separating at least one of perfluoromethane and nitrogen trifluoride from a mixture comprising perfluoromethane and/or nitrogen trifluoride. The process is conducted by contacting the mixture with at least one ionic liquid. In a preferred embodiment, the process is conducted by absorption or by extractive distillation wherein at least one ionic liquid is used as the absorbant or entraining agent, respectively.

BACKGROUND

Various gaseous fluorine-containing compounds are utilized in manufacturing processes that plasma-etch silicon-type materials in order to fabricate semiconductor devices. A major use of tetrafluoromethane ($CF_4$ or FC-14) is for plasma etching during semiconductor device fabrication. Plasma etchants interact with the surface of an integrated circuit wafer, modifying it so as to lay down the electrical pathways and provide for the surface functionalities that define the integrated surface. A major use of nitrogen trifluoride ($NF_3$) is as a "chemical vapor deposition" (CVD) chamber cleaning gas in semiconductor device manufacture. CVD chamber cleaning gases are used to form plasmas, which interact with the internal surfaces of semiconductor fabrication equipment to remove the various deposits that accumulate over time.

Perfluorinated chemicals such as $CF_4$ and $NF_3$ that are used in semiconductor manufacturing applications as etchant or cleaning gases are more commonly referred to as "electronic gases". Electronic gases having high purity are critical for such semiconductor device manufacture applications. It has been found that even very small amounts of impurities in these gases that enter semiconductor device manufacturing tools can result in wide line width, and thus less information per device.

The desire for greater precision and consistency of the effect that compounds such as $CF_4$ and $NF_3$ have during integrated circuit manufacture has made extremely high purities critical for such applications. The presence of any other compounds in the $CF_4$ or $NF_3$ is objectionable for most of the intended uses. It should be recognized that either $CF_4$ or $NF_3$ might in itself be considered an impurity if present in the product stream of the other. For example, even a 1 part-per-million-molar concentration of $CF_4$ would be considered an impurity in $NF_3$ where that $NF_3$ is to be used as a cleaning agent product. Similarly, even a 1 parts-per-million-molar concentration of $NF_3$ would be considered an impurity in $CF_4$ where that $CF_4$ is to be used as an etchant product. Processes that enable the manufacture of $CF_4$ or $NF_3$ products having purities that approach 99.999 molar percent purity are desirable, but processes that provide at least 99.9999 molar percent purity for electronic gas applications are preferred. Analytical methods for gauging such low concentrations of impurities in $CF_4$ and $NF_3$ products are available. For example, methods for analyzing low concentrations of $CF_4$ and other impurities in an $NF_3$ product are disclosed in the 1995 SEMI standards, pages 149-153, SEMI C3.39.91-Standard for Nitrogen Trifluoride. Alternately, techniques for analyzing the concentration of $CF_4$ and other impurities at low concentrations in FC-116, but which may also be applied to analysis of $NF_3$ and $CF_4$ products, are disclosed in "Examining Purification and Certification Strategies for High-Purity $C_2F_6$ Process Gas", Micro Magazine, April 1998, page 35.

Conventional processes for manufacturing $NF_3$, however, often produce $CF_4$ as a component in the $NF_3$ product stream. Because conventional processes are not able to separate the $CF_4$ from the $NF_3$ product, $NF_3$ products containing less than about 10 ppm-molar $CF_4$ are not available in spite of the desirability of lower concentrations of $CF_4$ in said $NF_3$ product.

Moreover, the presence of impurities, including but not limited to particulates, metals, moisture, and other halocarbons in the plasma etchant or cleaning gas, even when present at only the part-per-million level, increases the defect rate in the production of high-density integrated circuits. As a result, there has been increasing demand for higher purity etchant and cleaning gases, and an increasing market value for the materials having the required purity. Identification of offending components and methods for their removal consequently represent a significant aspect of preparing these gases, particularly fluorine-containing compounds, for use for such purpose.

Etchant and cleaning gases are not fully consumed by semiconductor manufacturing processes, but typically exit the integrated circuit fabrication equipment in finite concentrations. These fabrication equipment exhaust streams not only contain varying amounts of unreacted perfluorinated etchant and cleaning gases, but may also contain a variety of reaction products and air components, which include without limitation hydrogen fluoride (HF), tetrafluoroethylene ($C_2F_4$ or FC-1114), methyl fluoride ($CH_3F$ or HFC-41), trifluoromethane ($CHF_3$ or HFC-23), chlorotrifluoromethane ($CClF_3$ or CFC-13), nitrogen, oxygen, carbon dioxide, water, methane, ethane, propane and nitrous oxide ($N_2O$). Typically, this results in a stream containing a wide range of $CF_4$, $NF_3$, and other fluorinated impurities in a wide range of concentrations, and this exhaust stream may also contains relatively high volume concentrations, typically greater than 50 volume %, of inert carrier gases such as air, helium or nitrogen.

Exhaust streams coming off of processes in which gases such as $CF_4$ and $NF_3$ are used are also frequently combined with exhaust streams from other types of semiconductor manufacturing activities. These other activities can generate a variety of waste gases in their own right, such as hexafluoroethane ($C_2F_6$ or FC-116), octafluorocyclobutane (cyclic $C_4F_8$ or FC-C318), octafluoropropane ($C_3F_8$ or FC-218), sulfur hexafluoride ($SF_6$), pentafluoroethane ($C_2HF_5$ or HFC-125), trifluoromethane ($CHF_3$ or HFC-23), tetrafluoroethane ($C_2H_2F_4$, or HFC-134a or HFC-134) and difluoromethane ($CH_2F_2$ or HFC-32). The resulting combined exhaust stream consequently may contain a wide range of compounds and at widely varying concentrations.

Concerns over possible environmental impact of such materials and the high value-in-use of these materials has prompted a search for methods of recovering $CF_4$ or $NF_3$ from said exhaust streams of such processes. Conventional methods of recovering the components from such streams typically involve water washing the exhaust stream to remove the HF and HCl, then drying the stream using a variety of methods. Conventional methods for separating and recovering the fluorinated compounds from the large concentrations of inert carrier gases include use of semi-permeable membranes or adsorption of the fluorinated compounds into liquid solvents. However, a wide range of fluorinated organic and inorganic compounds typically still remain in the captured stream after such processing steps, making any $CF_4$ or $NF_3$ contained within unsuitable for reuse as electronic gases.

There is thus considerable interest in developing methods to capture fluorinated compounds that are present in manufacturing equipment exhaust streams, and in developing options for their disposition. A preferred disposition option is to repurify certain of the fluorinated components from these streams for reuse. Separation of several of these valuable fluorinated compounds is made difficult, however, due to the variety of fluorinated compounds that might be present in the combined exhaust gas stream from any given manufacturing site, and due to non-ideal interactions that exist between several of these compounds. For example, several of these compounds form azeotropes, azeotropic compositions, or azeotrope-like compositions with other compounds in these streams, making separation by conventional distillation at least difficult, if not impossible. The ability to separate and recover a $NF_3$ product that is substantially free of $CF_4$ and other fluorinated impurities, particularly where the $CF_4$ concentration in the $NF_3$ product is preferably less than 3, more preferably less than 1, ppm-molar, is thus of considerable commercial interest. The ability to separate and recover a $CF_4$ product that is substantially free of fluorinated impurities is also of considerable commercial interest.

Many of the fluorinated compounds used or that are produced in semiconductor process operations are extremely close-boiling in their separated and pure states. Compounds whose selectivities approach or equal 1.0 compared to $CF_4$ or $NF_3$ make their separation from said $CF_4$ or $NF_3$ by conventional distillation difficult. Separation of such mixtures is particularly problematic where it is desired that the recovered $CF_4$ or $NF_3$ product be substantially free of other fluorinated compounds and where the $CF_4$ or $NF_3$ product needs to be recovered from a first mixture with high recovery efficiency.

U.S. Pat. No. 6,458,249, which is incorporated in its entirety as a part hereof for all purposes, provides a process for separating $CF_4$ and $NF_3$ from each other, and from mixtures with other materials used in the electronics industry, by distilling a mixture comprising $NF_3$ and/or $CF_4$ in the presence of an entraining agent, such as nitrous oxide or hydrogen chloride. The use of a nitrous oxide entrainer requires cryogenic temperatures for achieving good separation. Hydrogen chloride is a strong acid that presents waste disposal problems. There thus remains a need for an environmentally suitable and energy efficient process for the separation of compounds such as $NF_3$ and/or $CF_4$.

SUMMARY

In one embodiment, this invention provides a process for separating nitrogen trifluoride or tetrafluoromethane from a mixture that comprises nitrogen trifluoride and tetrafluoromethane, by contacting the mixture with at least one ionic liquid in which one member of the group of nitrogen trifluoride and tetrafluoromethane is soluble to a different extent (such as more or less soluble) than the other member, and separating the lower-solubility member from the mixture.

In another embodiment, this invention provides a process for separating nitrogen trifluoride or tetrafluoromethane from a mixture that comprises nitrogen trifluoride, tetrafluoromethane and other compounds, by contacting the mixture with at least one ionic liquid in which one member of the group of nitrogen trifluoride and tetrafluoromethane is soluble to a different extent (such as more or less soluble) than either the other member of the group or another compound of the mixture, and separating the low solubility member of the group from the mixture.

An ionic liquid as used in this process is an ionic liquid that absorbs at least one component of a mixture, and facilitates the separation of a component from the mixture by steps, for example, such as absorption or extractive distillation.

BRIEF DESCRIPTION OF THE DRAWINGS

FIG. 1. shows a schematic diagram of a simple extractive distillation process.

DETAILED DESCRIPTION

The present invention relates to a process for separating $CF_4$ $NF_3$ from a variety of fluorinated compounds and from each other. One or more ionic liquids increase the efficiency of such separation by functioning, for example, as an absorbent in an absorber, or as an entrainer in an extractive distillation system by which the separation may be conducted.

In the description of this invention, the following definitional structure is provided for certain terminology as employed in various locations in the specification:

An "absorbent" is a compound that, when added to a mixture, interacts with the components in the mixture in a way that changes the relative volatilities of the components in the mixture to each other such that those components may then be separated by an absorption process. The absorbent is used in an "effective amount", which is an amount of the absorbent that, in the presence of a mixture of a desired product and an impurity, causes the volatility of the impurity to increase or decrease relative to that of the desired product sufficiently to allow separation of the impurity from the desired product. This may be accomplished, for example, by the formation from the impurity and the desired product of a lower- or higher-boiling azeotrope, azeotropic composition or azeotrope-like composition. The amount of the effective amount may vary depending on the conditions, such as temperature and/or pressure, in which the mixture exists. The separation may be performed, for example, by an absorption process.

An "absorber" is a device to conduct an absorption separation process in which an absorbent is added to aid in the separation of gaseous components of an azeotrope, an azeotropic composition or an azeotrope-like composition. The absorbant interacts selectively with (but does not react with) one or more components within the gas composition, as more particularly described in Section 13, "Distillation", in Perry's Chemical Engineers' Handbook, $7^{th}$ Ed., (McGraw-Hill, 1997).

An "alkane" or "alkane compound" is a saturated hydrocarbon having the general formula $C_nH_{2n+2}$, and may be a straight-chain, branched or cyclic.

An "alkene" or "alkene compound" is an unsaturated hydrocarbon that contains one or more carbon-carbon double bonds, and may be a straight-chain, branched or cyclic. An alkene requires a minimum of two carbons. A cyclic compound requires a minimum of three carbons.

An "aromatic" or "aromatic compound" includes benzene and compounds that resemble benzene in chemical behavior.

An "azeotrope" or "azeotropic composition" is a constant-boiling mixture of two or more substances that behaves as a single substance. An azeotropic composition may be characterized by the fact that the vapor produced by partial evaporation or distillation of the liquid has the same composition as the liquid from which it is evaporated or distilled, i.e. the mixture distills/refluxes without compositional change. Constant-boiling compositions are characterized as azeotropic because they exhibit either a maximum or minimum boiling point, as compared with that of the non-azeotropic mixture of the same components. Azeotropic compositions are also characterized by a minimum or a maximum in the vapor pressure relative to the vapor pressure as a function of composition at a constant temperature.

An "azeotrope-like composition" is a composition that has a constant-boiling characteristic, or a tendency not to fractionate upon boiling or evaporation. Therefore, the composition of the vapor formed is the same as or substantially the same as the original liquid composition. During boiling or evaporation, the liquid composition, if it changes at all, changes to only a minimal or negligible extent. An azeotrope-like composition can also be characterized by the area that is adjacent to the maximum or minimum vapor pressure in a plot of composition vapor pressure at a given temperature as a function of mole fraction of components in the composition. A composition is azeotrope-like if, after about 50 weight percent of an original composition is evaporated or boiled off to produce a remaining composition, the change between the original composition and the remaining composition is no more than about 6 weight %, and often is no more than about 3 weight %, relative to the original composition.

An azeptrope, azeotropic composition or azeotrope-like composition may also be characterized as a close-boiling, substantially constant-boiling or constant-boiling mixture that may appear under many guises, depending upon the existing conditions, as illustrated by the manner in which the following factors may apply:

1) At different pressures, the compositional content of these kinds of mixture will vary at least to some degree, as will the boiling point temperature. Thus, such a mixture represents a unique type of relationship between the components thereof but will typically have variable compositional content, which depends on temperature and/or pressure. Therefore, ranges of compositional content, rather than a fixed compositional content, are often used to define such a mixture.
2) These kinds of mixtures can be characterized by a boiling point at a given pressure rather than by a specific compositional content, the determination of which is limited by, and is only accurate as, the analytical equipment available to make the determination.
3) Both the boiling point and the weight (or mole) percent content of each component in these kinds of mixtures may change when the mixture is allowed to boil at different pressures. Thus, such a mixture may be defined in terms of the unique relationship that exists among the components thereof, or in terms of the exact weight (or mole) percentages of each component therein in terms of a fixed boiling point at a specific pressure.

"Azeotropic distillation" is a process in which a distillation column is operated under conditions to cause a mixture such as an azeotrope, azeotropic composition or azeotrope-like composition to form, and the formation thereof changes the relative volatility of the components therein to each other such that the components may be separated by distillation. Azeotropic distillations may occur where only the components of the mixture to be separated are distilled, or where an entraining agent is added that forms an azeotrope, azeotropic composition or azeotrope-like composition with one or more of the components of the initial mixture. Entraining agents that form an azeotrope, azeotropic composition or azeotrope-like composition with one of more of the components of the mixture to be separated, thus facilitating the separation of those components by distillation, also function as azeotroping agents or azeotropic entraining agents.

An "entraining agent" is a compound that, when added to a mixture, interacts with the components in the mixture in a way that changes the relative volatilities of the components in the mixture to each other such that those components may then be separated by a distillation process. The entraining agent is used in an "effective amount", which is an amount of the entraining agent that, in the presence of a mixture of a desired product and an impurity, causes the volatility of the impurity to increase or decrease relative to that of the desired product sufficiently to allow separation of the impurity from the desired product. This may be accomplished, for example, by the formation from the impurity and the desired product of a lower- or higher-boiling azeotrope, azeotropic composition or azeotrope-like composition. The amount of the effective amount may vary depending on the conditions, such as temperature and/or pressure, in which the mixture exists. The separation may be accomplished, for example, by an extractive distillation process.

"Extractive distillation" is a process in which an entraining agent is added to aid in the separation of components of a mixture such as an azeotrope, an azeotropic composition or an azeotrope-like composition, as more particularly described in sources such as Section 13, "Distillation", in Perry's Chemical Engineers' Handbook, $7^{th}$ Ed., (McGraw-Hill, 1997). The entrainer interacts selectively with (but does not react with) one or more components within the mixture, and is typically introduced at an upper feed point of a distillation column, while the mixture requiring separation is introduced at the same, or preferably a relatively lower, feed point of the column than the entraining agent. The entraining agent passes downwardly through trays or packing located in the column and exits the column bottoms with one or more components of the mixture to be separated. While in the presence of the entraining agent, at least one of the components to be separated becomes relatively more volatile compared to the other component(s) of the mixture, such that the more volatile component of the mixture exits the column overhead. Entraining agents that are fed to a distillation column at a point equal to, or higher than, the mixture to be separated, and that pass down through the column to enable a separation by distillation, also function as extractive agents or extractants.

A "high-boiling azeotrope" is an azeotrope, azeotropic composition or azeotrope-like composition that boils at a higher temperature at any given pressure than any one of the components therein would separately boil at that pressure. A high-boiling azeotrope may also be any azeotrope, azeotropic composition or azeotrope-like composition that has a lower vapor pressure at any given temperature than any one of the components therein would separately have at that temperature.

An "ionic liquid" is an organic salt that is fluid at about 100° C. or below, as more particularly described in *Science* (2003) 302:792-793. A "fluorinated ionic liquid" is an ionic liquid having at least one fluorine on either the cation or the anion. A "fluorinated cation" or "fluorinated anion" is a cation or anion, respectively, comprising at least one fluorine.

A "halogen" is bromine, iodine, chlorine or fluorine.

A "heteroaryl" group is an alkyl group having a heteroatom.

A "heteroatom" is an atom other than carbon in the structure of an alkanyl, alkenyl, cyclic or aromatic compound.

"High recovery efficiency" indicates that greater than 90 mol %, and preferably greater than 95 mol %, of a desired compound is recovered from a mixture of the compound with an impurity, such as when the $CF_4$ or $NF_3$ in a mixture is recovered as product substantially free of one or more fluorinated impurities.

An "impurity" is any undesired component in a mixture, such as a fluorinated compound other than $CF_4$ that is present in and thus forms a mixture with the $CF_4$ compound, or a fluorinated compound other than $NF_3$ that is present in and thus forms a mixture with the $NF_3$ compound.

A "low-boiling-azeotrope" is meant that an azeotropic or azeotrope-like composition boils at a lower temperature at any given pressure than any one of the compounds that comprise it would separately boil at that pressure. Alternately, by low-boiling azeotrope is meant any azeotropic or azeotrope-like composition that has a higher vapor pressure at any given temperature than the vapor pressure of any one of the compounds that comprise the azeotrope would separately have at that temperature.

"Optionally substituted with at least one member selected from the group consisting of", when referring to an alkane, alkene, alkoxy, fluoroalkoxy, perfluoroalkoxy, fluoroalkyl, perfluoroalkyl, aryl or heteroaryl radical or moiety, means that one or more hydrogens on a carbon chain of the radical or moiety may be independently substituted with one or more of the members of a recited group of substituents. For example, a substituted $-C_2H_5$ radical or moiety may, without limitation, be $-CF_2CF_3$, $-CH_2CH_2OH$ or $-CF_2CF_2I$ where the group or substituents consist of F, I and OH.

"Selectivity", $\alpha_{ij}$, with respect to components i and j in a mixture, is the ratio of the infinite dilution activity coefficient of component i to the infinite dilution activity coefficient of component j, component i and j being present at an infinite degree of dilution in the mixture as subjected to a separation process.

"Separating" or "to separate" refers to the removal of one or more components from a mixture. In various embodiments, separating or to separate may refer to the partial or complete removal of one or more components from a mixture. If further purification is required, one or more additional separation steps may be required to achieve complete removal. Additional separation steps, like initial separation steps, may be performed, for example, by processes such as distillation, gas stripping, chromatography and/or evaporation.

A $CF_4$ compound or a $NF_3$ compound is "substantially pure", or is "substantially free of impurity", when there is present in the compound another fluorinated species as an impurity in an amount of (a) less than 10 parts-per-million-by-volume (ppmv) or 10 parts-per-million-molar (ppm-molar), more preferably less than 1 ppmv or 1 ppm-molar, and most preferably less than 100 parts-per-billion-by-volume (ppbv) or 100 parts-per-billion-molar (ppb-molar); or (b) less than 10 parts-per-million-by-weight (ppmw), more preferably less than 1 ppmw, and most preferably less than 100 parts-per-billion-by-weight (ppbw).

A "vacuum" is a pressure less than 1 bar but greater than $10^{-4}$ bar for practical use in separation equipment.

$CF_4$ and $NF_3$ are known compounds that may be separated from a variety of fluorinated compounds and/or from each other such that the CF4 or $NF_3$ is recovered in substantially pure from and with high recovery efficiency. This invention involves the use of an ionic liquid to enhance the efficiency of the separation. As discussed below, various suitable methods for performing the separation include extractive distillation, in which an ionic liquid serves as an entraining agent; or absorption, in which an ionic liquid serves as an absorbent. An ionic liquid suitable for use for such purpose will interact with at least one of the components in a mixture in which $CF_4$ and/or $NF_3$ are present to increase the separation efficiency, and can in principle be any ionic liquid that absorbs at least one component of such a mixture. Preferably, to maximize separation efficiency, the ionic liquid should have high solubility for at least one component of the mixture.

Ionic liquids are organic compounds that are liquid at room temperature (approximately 25° C.). They differ from most salts in that they have very low melting points, they tend to be liquid over a wide temperature range, and have been shown to have high heat capacities. Ionic liquids have essentially no vapor pressure, and they can either be neutral, acidic or basic. The properties of an ionic liquid can be tailored by varying the cation and anion. A cation or anion of an ionic liquid useful for the present invention can in principle be any cation or anion such that the cation and anion together form an organic salt that is liquid at or below about 100° C.

Many ionic liquids are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form the ionic liquid. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups, since groups larger than this may produce low melting solids rather than ionic liquids. Various triarylphosphines, thioethers and cyclic and non-cyclic quaternary ammonium salts may also been used for this purpose. Counterions that may be used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal-containing anions.

Ionic liquids may also be synthesized by salt metathesis, by an acid-base neutralization reaction or by quaternizing a selected nitrogen-containing compound; or they may be obtained commercially from several companies such as Merck (Darmstadt, Germany) or BASF (Mount Olive, N.J.).

Representative examples of ionic liquids useful herein included among those that are described in sources such as *J. Chem. Tech. Biotechnol.*, 68:351-356 (1997); *Chem. Ind.*, 68:249-263 (1996); *J. Phys. Condensed Matter*, 5: (supp 34B):B99-B106 (1993); *Chemical and Engineering News*, Mar. 30, 1998, 32-37; *J. Mater. Chem.*, 8:2627-2636 (1998); *Chem. Rev.*, 99:2071-2084 (1999); and WO 05/113,702 (and references therein cited). In one embodiment, a library, i.e. a combinatorial library, of ionic liquids may be prepared, for example, by preparing various alkyl derivatives of a quaternary ammonium cation, and varying the associated anions. The acidity of the ionic liquids can be adjusted by varying the molar equivalents and type and combinations of Lewis acids.

In the various embodiments of this invention, an ionic liquid suitable for use may have a cation selected from the following formulae:

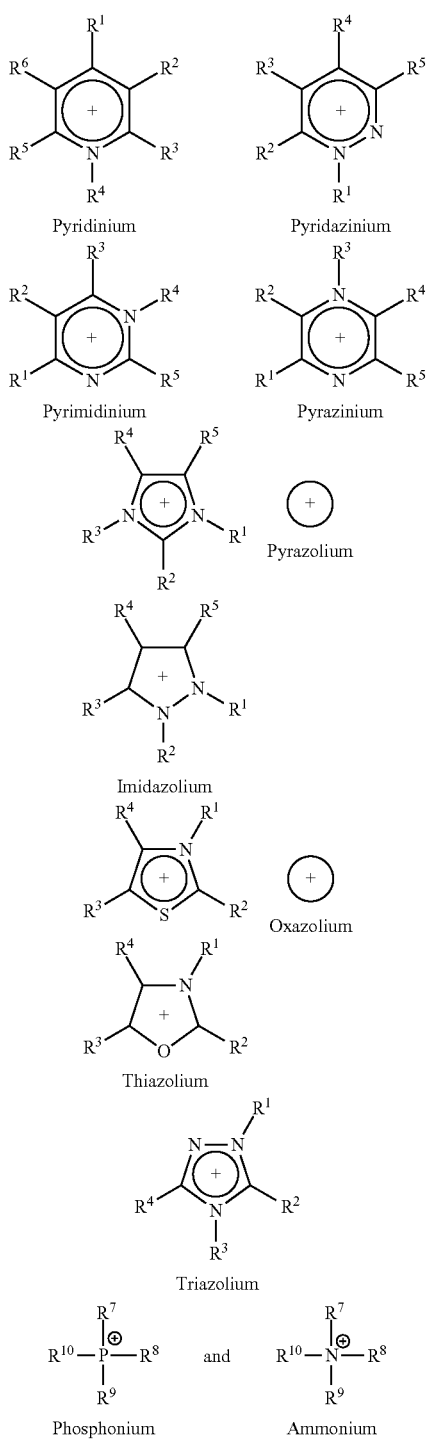

wherein $R^1$, $R^2$, $R^3$, $R^4$, $R^5$ and $R^6$ are independently selected from the group consisting of:
(i) H
(ii) halogen
(iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(v) $C_6$ to $C_{20}$ unsubstituted aryl, or $C_3$ to $C_{25}$ unsubstituted heteroaryl having one to three heteroatoms independently selected from the group consisting of O, N, Si and S; and
(vi) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(1) —$CH_3$, —$C_2H_5$, or $C_3$ to $C_{25}$ straight-chain, branched or cyclic alkane or alkene, optionally substituted with at least one member selected from the group consisting of Cl, Br, F I, OH, $NH_2$ and SH,
(2) OH,
(3) $NH_2$, and
(4) SH;
$R^7$, $R^8$, $R^9$, and $R^{10}$ are independently selected from the group consisting of:
(vii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(viii) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(ix) $C_6$ to $C_{25}$ unsubstituted aryl, or $C_3$ to $C_{25}$ unsubstituted heteroaryl having one to three heteroatoms independently selected from the group consisting of O, N, Si and S; and
(x) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
(1) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
(2) OH,
(3) $NH_2$, and
(4) SH; and
wherein optionally at least two of $R^1$, $R^2$, $R^3$, $R^4$, $R^5$, $R^6 R^7$, $R^8$, $R^9$, and $R^{10}$ can together form a cyclic or bicyclic alkanyl or alkenyl group.

In another embodiment, ionic liquids useful for the invention comprise fluorinated cations wherein at least one member selected from $R^1$, $R^2$, $R^3$, $R^4$, $R^5$, $R^6$, $R^7$, $R^8$, $R^9$ and $R^{10}$ comprises $F^-$.

In one embodiment, ionic liquids have anions selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$; and preferably any fluorinated anion. Fluorinated anions of the invention include $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$,

[CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$; and F$^-$. In another embodiment, ionic liquids comprise a cation selected from the group consisting of pyridinium, pyridazinium, pyrimidinium, pyrazinium, imidazolium, pyrazolium, thiazolium, oxazolium, triazolium, phosphonium, and ammonium as defined above; and an anion selected from the group consisting of [CH$_3$CO$_2$]$^-$, [HSO$_4$]$^-$, [CH$_3$OSO$_3$]$^-$, [C$_2$H$_5$OSO$_3$]$^-$, [AlCl$_4$]$^-$, [CO$_3$]$^{2-}$, [HCO$_3$]$^-$, [NO$_2$]$^-$, [NO$_3$]$^-$, [SO$_4$]$^{2-}$, [PO$_4$]$^{3-}$, [HPO$_4$]$^{2-}$, [H$_2$PO$_4$]$^-$, [HSO$_3$]$^-$, [CuCl$_2$]$^-$, Cl$^-$, Br$^-$, I$^-$, SCN$^-$; and any fluorinated anion. In yet another embodiment, ionic liquids comprise a cation selected from the group consisting of pyridinium, pyridazinium, pyrimidinium, pyrazinium, imidazolium, pyrazolium, thiazolium, oxazolium, triazolium, phosphonium, and ammonium as defined above; and an anion selected from the group consisting of [BF$_4$]$^-$, [PF$_6$]$^-$, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$, and F$^-$.

In still another embodiment, ionic liquids comprise a cation selected from the group consisting of pyridinium, pyridazinium, pyrimidinium, pyrazinium, imidazolium, pyrazolium, thiazolium, oxazolium, triazolium, phosphonium, and ammonium as defined above, wherein at least one member selected from R$^1$, R$^2$, R$^3$, R$^4$, R$^5$, R$^6$, R$^7$, R$^8$, R$^9$, and R$^{10}$ comprises F$^-$; and an anion selected from the group consisting of [CH$_3$CO$_2$]$^-$, [HSO$_4$]$^-$, [CH$_3$OSO$_3$]$^-$, [C$_2$H$_5$OSO$_3$]$^-$, [AlCl$_4$]$^-$, [CO$_3$]$^{2-}$, [HCO$_3$]$^-$, [NO$_2$]$^-$, [NO$_3$]$^-$, [SO$_4$]$^{2-}$, [PO$_4$]$^{3-}$, [HPO$_4$]$^{2-}$, [H$_2$PO$_4$]$^-$, [HSO$_3$]$^-$, [CuCl$_2$]$^-$, Cl$^-$, Br$^-$, I$^-$, SCN$^-$; and any fluorinated anion. In still another embodiment, ionic liquids comprise a cation selected from the group consisting of pyridinium, pyridazinium, pyrimidinium, pyrazinium, imidazolium, pyrazolium, thiazolium, oxazolium, triazolium, phosphonium, and ammonium as defined above, wherein at least one member selected from R$^1$, R$^2$, R$^3$, R$^4$, R$^5$, R$^6$, R$^7$, R$^8$, R$^9$, and R$^{10}$ comprises F$^-$; and an anion selected from the group consisting of [BF$_4$]$^-$, [PF$_6$]$^-$, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$, and F$^-$.

In a more specific embodiment, the at least one ionic liquid comprises 1-butyl-3-methylimidazolium, 1,2-dimethyl-3-propylimidazolium, 1-octyl-3-methylimidazolium, 1,3-dioctylimidazolium, 1-ethyl-3-methylimidazolium, 1-dodecyl-3-methylimidazolium, 1-heptyl-3-methylimidazolium, 3-methyl-1-propylpyridinium, 1-butyl-3-methylpyridinium, tetradecyl(trihexyl)phosphonium, or tributes(tetradecyl) phosphonium as the cation and an anion selected from the group consisting of [CH$_3$CO$_2$]$^-$, [HSO$_4$]$^-$, [CH$_3$OSO$_3$]$^-$, [C$_2$H$_5$OSO$_3$]$^-$, [AlCl$_4$]$^-$, [CO$_3$]$^{2-}$, [HCO$_3$]$^-$, [NO$_2$]$^-$, [NO$_3$]$^-$, [SO$_4$]$^{2-}$, [PO$_4$]$^{3-}$, [HPO$_4$]$^{2-}$, [H$_2$PO$_4$]$^-$, [HSO$_3$]$^-$, [CuCl$_2$]$^-$, Cl$^-$, Br$^-$, I$^-$, SCN$^-$, [BF$_4$]$^-$, [PF$_6$]$^-$, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, and [(CF$_3$CFHCF$_2$SO$_2$)$_2$N]$^-$.

In an even more specific embodiment, the at least one ionic liquid is selected from the group consisting of 1-butyl-3-methylimidazolium hexafluorophosphate [bmim][PF$_6$], 1-butyl-3-methylimidazolium tetrafluoroborate [bmim][BF$_4$], 1,2-dimethyl-3-propylimidazolium tris(trifluoromethylsulfonyl)methide [dmpim][TMeM], 1-octyl-3-methylimidazolium iodide [omim][I], 1,3-dioctylimidazolium iodide [doim][I], 1-ethyl-3-methylimidazolium bis(pentafluoroethylsulfonyl)imide [emim][BEI], 1,2-dimethyl-3-propylimidazolium bis(trifluoromethylsulfonyl)imide [dmpim][BMeI], 3-methyl-1-propylpyridinium bis(trifluoromethylsulfonyl)imide [pmpy][BMeI], 1-ethyl-3-methylimidazolium hexafluorophosphate [emim][PF$_6$], 1-ethyl-3-methylimidazolium bis(trifluoroethylsulfonyl)imide [emim][BMeI], 1-butyl-3-methylpyridinium bis(trifluoromethylsulfonyl)imide [bmpy][BMeI], 1-ethyl-3-methylimidazolium 1,1,2,2-tetrafluoroethanesulfonate [emim][TFES], 1-butyl-3-methylimidazolium 1,1,2,2-tetrafluoroethanesulfonate [bmim][TFES], 1-dodecyl-3-methylimidazolium 1,1,2,2-tetrafluoroethanesulfonate [dmim][TFES], 1-heptyl-3-methylimidazolium 1,1,2,2-tetrafluoroethanesulfonate [hmim][TFES], 1-butyl-3-methylimidazolium acetate [bmim][Ac], 1-butyl-3-methylimidazolium 2-(1,2,2,2-tetrafluoroethoxy)-1,1,2,2-tetrafluoroethanesulfonate [bmim][FS], 1-butyl-3-methylimidazolium 1,1,2,3,3,3-hexafluoropropanesulfonate [bmim][HFPS], 1-butyl-3-methylimidazolium methyl sulfonate [bmim][MeSO$_4$], 1-butyl-3-methylimidazolium thiocyanate [bmim][SCN], 1-butyl-3-methylimidazolium 1,1,2-trifluoro-2-(perfluoroethoxy)ethanesulfonate [bmim][TPES], 1-butyl-3-methylimidazolium 1,1,2-trifluoro-2-(trifluoromethoxy)ethanesulfonate [bmim][TTES], 1-butyl-3-methylimidazolium 1,1,2-trifluoro-2-(trifluoromethoxy)ethanesulfonate [bmim][TTES], 1-butyl-3-methylimidazolium 1,1,2-trifluoro-2-(perfluoroethoxy)ethanesulfonate [bmim][TPES], 1-ethyl-3-methylimidazolium bis(pentafluoroethylsulfonyl)imide [emim][BEI], 1-butyl-3-methylimidazolium 1,1,2,3,3-hexafluoropropanesulfonate [bmim][HFPS], tetradecyl(trihexyl)phosphonium 1,1,2-trifluoro-2-(perfluoroethoxy)ethanesulfonate [6,6,6,14-P][TPES], tributyl(tetradecyl)phosphonium 1,1,2,3,3,3-hexafluoropropanesulfonate [4,4,4,14-P][HFPS].

In various other embodiments of this invention, an ionic liquid formed by selecting any of the individual cations described or disclosed herein, and by selecting any of the individual anions described or disclosed herein, may be used for the purpose of effecting the separation of either CF$_4$ or NF$_3$ as a component from a mixture in which it is contained. Correspondingly, in yet other embodiments, a subgroup of ionic liquids formed by selecting (i) a subgroup of any size of cations, taken from the total group of cations described and disclosed herein in all the various different combinations of the individual members of that total group, and (ii) a subgroup of any size of anions, taken from the total group of anions described and disclosed herein in all the various different combinations of the individual members of that total group, may be used for the purpose of effecting the separation of either CF$_4$ or NF$_3$ as a component from a mixture in which it is contained. In forming an ionic liquid, or a subgroup of ionic liquids, by making selections as aforesaid, the ionic liquid or subgroup will be used in the absence of the members of the group of cations and/or anions that are omitted from the total group thereof to make the selection, and, if desirable, the selection may thus be made in terms of the members of the total group that are omitted from use rather than the members of the group that are included for use.

Systems of particular interest in this invention are those in which either $CF_4$ or $NF_3$ is separated as a component from a mixture in which it is contained by the addition to the mixture of at least one fluorinated ionic liquid, such as an ionic liquid that has a fluorinated anion, a fluorinated cation or both, in view of what may be useful interactions between and/or among the various fluorinated species that may increase the solubility of either $CF_4$ or $NF_3$ in an ionic liquid.

$CF_4$ and $NF_3$ are known compounds that may be obtained from a variety of suitable manufacturing processes or sources. $CF_4$ may, for example, be produced by reacting a chlorocarbon or chlorofluorocarbon with HF, and $NF_3$ may be produced by reacting ammonia ($NH_3$) with elemental fluorine ($F_2$). Often, a process that produces or uses one of these compounds produces the other compound as an impurity, and one is then presented with a mixture of the two compounds and the resulting need to separate them and recover one from the other. $NF_3$ and $CF_4$, in their separated and pure states, have normal boiling points of −129.1 and −128.1° C., respectively. These close boiling points alone would make efficient separation of $NF_3$ and $CF_4$ by conventional distillation extremely difficult. In addition, however, mixtures of $NF_3$ and $CF_4$ form azeotropes, azeotropic compositions or azeotrope-like compositions over a range of temperatures and pressures, which makes their complete separation by conventional distillation extremely difficult if not essentially impossible.

When attempting to separate $CF_4$ and $NF_3$ from each other by conventional distillation, the azeotropes, azeotropic compositions or azeotrope-like compositions formed by those compounds can be used to achieve partial purification. A conventional distillation column may, for example, be operated at a pressure and temperature that causes an azeotrope, azeotropic composition or azeotrope-like composition to form. If the quantity of $NF_3$ versus $CF_4$ in the column is greater than that in the azeotrope, azeotropic composition or azeotrope-like composition, a $NF_3$ product can be removed from the bottom of the column with the $CF_4$ concentration in it reduced compared to the $CF_4$ concentration in the $NF_3/CF_4$ starting mixture, while the azeotrope, azeotropic composition or azeotrope-like composition is removed from the top of the column. Conversely, if the quantity of $CF_4$ versus $NF_3$ in the column is greater than that in the azeotrope, azeotropic composition or azeotrope-like composition, a $CF_4$ product can be removed from the bottom of the column with the $NF_3$ concentration in it reduced compared to the $NF_3$ concentration in the $NF_3/CF_4$ starting mixture, while the azeotrope, azeotropic composition or azeotrope-like composition is removed from the top of the column. Obtaining a $NF_3$ product stream having a reduced $CF_4$ concentration, or obtaining a $CF_4$ product stream having a reduced $NF_3$ concentration, in a single distillation would require starting with a composition higher in $NF_3$ or $CF_4$, respectively, than the azeotrope, azeotropic composition or azeotrope-like composition, but some portion of the $NF_3$ or $CF_4$ respectively would necessarily remain therein in the form of the $NF_3/CF_4$ azeotrope, azeotropic composition or azeotrope-like composition.

$NF_3$ can also be partially separated from $CF_4$ by a series of multiple distillations performed at alternately higher and lower pressures that involve forming low-boiling, high-pressure azeotropes, azeotropic compositions or azeotrope-like compositions of $NF_3$ and $CF_4$ in a conventional distillation column by giving effect to the changes in the $NF_3/CF_4$ azeotrope, azeotropic composition or azeotrope-like composition that occur with pressure. By taking the overhead distillate from a column that is operated under conditions such that one component is in excess to the azeotrope, azeotropic composition or azeotrope-like composition (a first distillation), then feeding that distillate to a column operated under conditions such that the other component is in excess of the azeotrope, azeotropic composition or azeotrope-like composition (a second distillation), then feeding the distillate from the second distillation to a column where the sequence is repeated (that is, where the next column is again operated under conditions such that the first component is in excess), it is possible to produce a bottoms product of $NF_3$ from one distillation, and of $CF_4$ from a second distillation, each of which has had the concentration of the other component reduced compared to a first mixture containing $NF_3$ and $CF_4$. This separation by "pressure-swing" distillation is possible only due to the unusual compositional change of the azeotrope, azeotropic composition or azeotrope-like composition with pressure or temperature. However, in these cases where only the relative volatility of the $NF_3/CF_4$ azeotrope, azeotropic composition or azeotrope-like composition compared to the individual $NF_3$ or $CF_4$ component present in excess of the azeotrope, azeotropic composition or azeotrope-like composition is used as the basis for their separation, such separations would require tall and expensive distillation columns, and it would still be extremely difficult, if not essentially impossible, to produce a substantially pure $NF_3$ or $CF_4$ product from a $NF_3/CF_4$ starting mixture.

Because of the difficulties in using a conventional distillation process to separate either CF4 or NF3 from a mixture thereof, the process of this invention involves improving the efficiency of the separation effort by contacting the mixture with at least one ionic liquid. This is advantageous because at least one of the components of the mixture will be less soluble in the ionic liquid than the other component(s), and preferably much less soluble. This difference in solubility facilitates the separation of the lower-solubility component from the mixture because when that component is removed, such as by volatilization, the more-soluble component will be removed to a more limited extent, and will preferably not be removed at all, because to the extent that it is soluble in the ionic liquid, it will tend to remain in, and not be removed from, the mixture.

The process of this invention may be performed, for example, by a technique such as extractive distillation. In extractive distillation, as in conventional distillation, at least one component of the mixture is caused, through temperature and pressure control, to be volatilized, and the volatilized component(s) is captured in a separate stream in which it is condensed apart from, and is thus removed from, the mixture. In extractive distillation, however, there is added to the mixture a miscible, high boiling, relatively nonvolatile component, the entraining agent, that has low latent heat of vaporization, does not form an azeotrope with any of the components in the mixture, and does not chemically react with any of the components in the mixture. The entraining agent is specially chosen to interact differently with the various components of the mixture, thereby altering their relative volatilities and "breaking" any azeotrope, azeotropic composition or azeotrope-like composition in which they would otherwise exist. The entraining agent is chosen to be a substance in which one or more of the components of the mixture is more soluble, and preferably much more soluble, than at least one other component of the mixture. A component that is less soluble in the entraining agent may, as a result, be more easily volatilized and separated from the mixture than a component that is more soluble in the entraining agent. The tendency that the components of an azeotrope, azeotropic composition or azeotrope-like composition would ordinarily have to volatilize in the essentially the same compositional ratio as they possess in liquid from is thus altered by the presence of the entraining agent, which, by solubilizing at least one component of the mixture to a greater extent than at least one other component, causes a corresponding change in the compositional content of the stream of volatiles liberated from the mixture at a selected temperature and pressure. The component(s) that are caused to be more volatile than others by the presence of the entraining agent in the mixture are then removed from the mixture as vapor in much higher concentration than the other components at the selected temperature and pressure. The more soluble, less volatile component(s) remain in the mixture with the entraining agent, and another criterion for selection of the entraining agent is that it be a substance that is easily separated from the remaining high-solubility, low-volatility component(s) of the mixture.

In various embodiments, it may be desirable to evaluate as the entraining agent a substance that causes the lower-boiling of two components in a mixture to become the more volatile of the two components as well. For example, a substance having greater chemical similarity to the higher-boiling of two components than to the lower-boiling may be evaluated for use as the entraining agent in such an embodiment. In various other embodiments, criteria that may be considered in evaluating a substance for selection as an entraining agent is whether the substance causes a positive deviation from Raoult's law with the lower-boiling of two components, or causes a negative deviation from Raoult's law with the higher-boiling of the two components.

When the separation process of this invention is performed by extractive distillation, an ionic liquid is used as an entraining agent. Mixtures of entraining agents, and thus mixtures of ionic liquids as entraining agents, may also be useful for achieving a desired extent of separation. In one embodiment, a mixture of entraining agents may be selected wherein one entraining agent has a high selectivity for the higher-volatility of the two components, and the other entraining agent has a high capacity to solubilize that component. In another embodiment, a mixture of ionic liquids may be used to separate the components of a mixture comprising at least two hydrofluorocarbon compounds by using multiple, discrete separation steps.

When the separation process of this invention is performed by extractive distillation, it may be advantageously performed in a distillation column such as is shown in the schematic diagram of FIG. 1. In the column of FIG. 1, separator elements 1 are used for the separation from the entraining agent of the top product, which is the mixture component that is made more volatile (less soluble) by the presence of the entraining agent in the mixture. Use of an ionic liquid as the entraining agent has the advantage of essentially eliminating the presence of the entraining agent in the overhead product 7 because of the negligible volatility of an ionic liquid. The overhead or distillate stream exiting the column may be condensed using reflux condensers. At least a portion of this condensed stream can be returned to the top of the column as reflux, and the remainder recovered as product or for optional processing. The ratio of the condensed material that is returned to the top of the column as reflux to the material removed as distillate is commonly referred to as the reflux ratio.

The flow of the entraining agent enters at inlet 2, which is preferably located in the enriching section close to the top of the column below the condenser, or at the bottom of the rectifying section, wherein any amount of the entraining agent that has unexpectedly volatilized is separated from the higher-volatility component of the mixture. The ionic liquid as entraining agent then proceeds in a countercurrent flow direction downward in the column relative to the upward flow of the higher-volatility component, and perhaps other components of the mixture to be separated. The mixture enters at inlet 4, above the stripping section, where any of the higher-volatility component that is still admixed with the entraining agent is finally vaporized. The inlet feed of the mixture to be separated may be in liquid or gaseous form, and, if the mixture is in liquid form when fed into the column, the higher-volatility component(s) thereof will be volatilzed by the temperature and pressure conditions of the column, which will have been selected for that purpose. The vapors moving upward in the column are continuously enriched in content of the higher-volatility component of the mixture, and the liquid moving downward in the column is continuously depleted in content of that higher-volatility component.

Separator elements 3 and 5 contain a useful number of stages along the height of the column at which there is thorough gas-liquid contacting, which is desirable for the purpose of obtaining extensive separation of a higher-volatility component, which exits the column as the overhead product 7, from a lower-volatility component, which exits the column together with the entraining agent as the bottom product 6. Separator elements can be either plates, or ordered or disordered packings. In either event, the purpose is to provide a downward cascade of the liquid entraining agent to contact the rising stream of vaporized high-volatility component. If plates are used, the liquid may flow over the edge of one plate onto another, or the liquid may flow through the same holes in the plates through which the volatilized component rises. In either case, the objective is to achieve maximum residence time of gas-liquid contact consistent with providing a rate of upward vapor flow that is high enough to prevent the column from being flooded by the downcoming liquid, but is not so high that the vapor is pushed out of the column without sufficient time to contact the liquid.

There is, in terms of the amount of the mixture to be separated, a minimum amount of the entraining agent that is needed to "break" any azeotrope, azeotropic composition or azeotrope-like composition that may exist, and enable the separation of at least one of the components from the mixture from the others in a yield and at a rate that is commercially feasible. In a ratio of the amount of entraining agent to the amount of feed, where the amount of entraining agent used in the ratio is the minimum amount described above, the value of the ratio may be set in the range of about 2 to about 4. Although feed ratios above 5 are sometimes found to offer no particular advantage in terms of being able to reduce the number of stages in a column, higher or lower feed ratios may be used herein as circumstances dictate.

The entraining agent is then removed from the mixture together with the higher-volatility component in a separate step, and is recycled to the column for re-entry into the column at inlet 2. The entraining agent may be separated from the bottom product 6 using various separating operations including regeneration by simple evaporation. Thin film evaporators, such as falling-film or rotary evaporators, are commonly used for continuous evaporation. In discontinuous concentration processes, two evaporator stages are run alternately so that regenerated ionic liquid, as entraining agent, can be returned continuously to the distillation column. The entraining agent can also be regenerated by means of a stripping column since the vapor pressure of the ionic liquid is essentially zero. An alternative means of recovering an ionic liquid as entraining agent takes advantage of the fact that many ionic liquids can solidify below 0° C. In these cases, low cost separation of the ionic liquid can be achieved by cooling to form a solid phase. The bottom product can also be precipitated using techniques such as cooling, evaporative, or vacuum crystallization.

For example, in one embodiment of a process as provided herein, (a) a mixture of $CF_4$ and $NF_3$ may be contacted with an ionic liquid to form a second mixture, (b) the second mixture may be processed by distillation, (c) $CF_4$ may be recovered as a distillation-column overhead stream, and (d) $NF_3$ and an ionic liquid may be recovered as a distillation-column bottom stream. Conversely, in another embodiment, (a) a mixture of $CF_4$ and $NF_3$ may be contacted with an ionic liquid to form a second mixture, (b) the second mixture may be processed by distillation, (c) $NF_3$ may be recovered as a distillation-column overhead stream, and (d) $CF_4$ and an ionic liquid may be recovered as a distillation-column bottom stream.

These and other aspects of extractive distillation are further discussed in well-known sources such as Perry's Chemical Engineers' Handbook, $7^{th}$ Ed. (Section 13, "Distillation", McGraw-Hill, 1997). When the separation process of this invention is performed by an absorption technique, equipment and practices similar to those described above for extractive distillation may be employed.

When the separation process of this invention is performed by extractive distillation, more than one distillation column may be required in systems in which a mixture contains multiple components to be separated. For example, non-close-boiling components may be separated and removed from the mixture using a first distillation column, and an azeotrope, azeotropic composition or azeotrope-like composition can then be separated using a second distillation column. An ionic liquid may be used as an entraining agent for one or both of the distillation columns. For example, where it is desirable to separate either $CF_4$ or $NF_3$ using one ionic liquid, one of the components may be recovered from the top of the column whereas the second component and ionic liquid can be recovered from the bottom of the column. The mixture comprising the second component and the ionic liquid can then be separated using a second distillation column (or flash tank); the second component can be recovered from the top of the second column (or flash tank), and the ionic liquid can be recovered from the bottom of the column (or flash tank) and recycled back to the first distillation column.

The ability to separate a binary mixture of two components i and j by distillation can be determined by calculating their selectivity. The closer the selectivity is to the value of one, the more difficult it is for the components of the mixture to be separated by conventional distillation. Therefore, an extractive distillation method may be used to enhance the separation efficiency. In extractive distillation, an entraining agent influences the separation by selectively absorbing or dissolving one or more of the components in the mixture. According to the present invention, the selectivity of an ionic liquid for a binary mixture composed of i and j is defined as the ratio of the infinite activity coefficient of component i to the infinite activity coefficient of component j, where components i and j are present at an infinite degree of dilution in the ionic liquid entraining agent. In general the selectivity can be greater than or less than 1 depending on whether the low boiler or high boiler is in the numerator. Normally the low boiler is placed in the numerator so that the selectivity is shown as a value greater than 1. In order to achieve separation, a selectivity of greater than about 1.0 is required. In one embodiment of the invention, the addition of an ionic liquid to the mixture provides a selectivity greater than about 1.5; and in other embodiments of the invention, the addition of an ionic liquid to the mixture provides a selectivity greater than about 3.0 or greater than about 5.0.

When the separation process of this invention is performed by extractive distillation, the individual components of the mixture to be separated may have respective concentrations ranging from about 0.05 to about 99.95 mole percent relative to the total weight of all components in the mixture plus the entraining agent depending on their location at any particular time in the column, at which location and time they may be subjected to a temperature in the range of from the reboiler temperature to the condenser temperature, and a pressure in the range of from vacuum to the critical pressure.

Extractive distillation processes operate at varying feed, reboiler, and condenser temperatures depending on the appropriate conditions for optimum separation. A typical extractive distillation process might operate with a condenser and or feed composition chilled by water to a temperature of 5 to 10° C., or chilled by brine or ethylene glycol to even lower temperatures of 0 to −40° C. In some cases, if the extractive distillation column operates at close to the normal boiling point of a compound at about 1 atmosphere pressure, the feed and or the condenser may cool the gas to even lower temperatures of −40 to −80° C. The reboiler can operate over a wide temperature range depending on the operating pressure of the column and the identity of the compound(s) being separated, which in the case of fluorinated compound could be a temperature range of from about −80 to about 240° C. The operating pressure of the distillation system may range from about 0.10 to about 3.45 MPa (about 15 to 500 psia), normally from about 0.35 to about 2.76 MPa 50 to 400 psia). Typically, an increase in the entraining agent feed rate relative to the feed rate of the mixture to be separated causes an increase in the purity of the product to be recovered with regard to those compound(s) being removed. Normally, increasing the reflux ratio results in increased distillate stream purity, but generally the reflux ratio ranges between 1/1 to 200/1. The temperature of the condenser, which is located adjacent to the top of the column, is normally sufficient to substantially fully condense the distillate that is exiting from the top of the column, or is that temperature required to achieve the desired reflux ratio by partial condensation.

The following examples are presented to illustrate the advantages of the present invention and to assist one of ordinary skill in making and using the same. These examples are not intended in any way otherwise to limit the scope of the disclosure or the appended claims. The operation of the invention is illustrated by studies related to the solubility of $CF_4$ and $NF_3$ in ionic liquids. Centigrade is abbreviated "C", and Kelvin is abbreviated "K".

General Methods and Materials

1-Butyl-3-methylimidazolium hexafluorophosphate ([bmim][PF$_6$], $C_8H_{15}N_2F_6P$, molecular weight 284 g mol$^{-1}$), was obtained from Fluka Chemika (may be obtained from Sigma-Aldrich, St. Louis, Mo.) with a purity of >97%. Tetrafluoromethane (FC-14, $CF_4$, molecular weight 88.005 g mol$^{-1}$) and nitrogen trifluoride ($NF_3$, molecular weight 71.019 g mol$^{-1}$), were obtained from DuPont Fluorochemicals (Wilmington, Del.), with a minimum purity of 99.99%.

The gas solubility measurements were made using a glass equilibrium cell (E. W. Slocum, Ind. Eng. Chem. Fundam., 14, 126, 1975). The glass equilibrium cell has a known volume and is agitated so that the upper phase (gas or liquid) mixes into the lower liquid phase. A known amount of ionic liquid is loaded into the cell and evacuated under heating to degas and remove any residual water in the ionic liquid. Knowing the density of the ionic liquid, the volume of the ionic liquid can be calculated, and the difference from the initial glass cell volume used to calculate the vapor space volume. A known amount of gas is fed into the cell and the temperature is held constant with a circulating oil bath. The pressure of the cell is measured and recorded. When the pressure is determined to no longer change, the cell is at equilibrium and the amount of gas absorbed is calculated by taking into account the amount of gas in the equilibrium cell vapor space. Details of the experimental equipment and procedures have been published (W. Schotte, *Ind. Eng. Chem. Process Des. Dev.*, 19, 432-439, 1980).

EXAMPLE 1

Separation of a Mixture Comprising Tetrafluoromethane (FC-14) and Nitrogen Trifluoride ($NF_3$)

This example focuses on the thermodynamic properties at the infinite dilution state. Activity coefficients at infinite dilution $\gamma^\infty$ and Henry's law constants $k_H$ were determined for FC-14 and $NF_3$ in [bmim][$PF_6$].

To obtain the Henry's law constants, $k_H$, the solubility data were analyzed. The Henry's constant is directly related to the excess chemical potential of solute at infinite dilution $$k_H(T, P) = \exp\frac{\mu_1^\infty - \mu_1^0}{RT}, \quad (1)$$

where $\mu_1^\infty$ is the chemical potential of the solute at the infinitely dilute solution state (in the present case, at the system T and P→0), and $\mu_1^0$ is the chemical potential referring to the pure gas (species 1) at the system T and at a pressure of 1 atm. Henry's constant, $k_H$, should be understood as being normalized (or dimensionless) with a proper standard state pressure (or 1 atm).

The Henry's law constant was obtained from the experimental solubility data shown in Examples 2 and 3 using the following relation:

$$k_H = \lim_{x_1 \to 0} \frac{f(T, P, y_1)}{x_1} \approx \left(\frac{df}{dx_1}\right)_{x_1=0}. \quad (2)$$

where f is the vapor phase fugacity of the pure gas ($y_1=1$) and can be calculated by proper equation-of-state model (Lemmon, E. W.; McLinden, M. O.; Huber, M. L. NIST reference fluid thermodynamic and transport properties—REFPROP, version 7.0, users' guide. U.S. Department of Commerce, Technology Administration, National Institute of Standards and Technology, Standard Reference Data Program, Gaithersburg, Md., 2002.) at a given experimental (T, P). The fugacity was fitted to a second-order polynomial of $x_1$ in order to use eq (2). The Henry's law constants thus obtained for the present system are shown in Table 1.

The relationship between the Henry's law constant, $k_H$, and the activity coefficient at infinite dilution, $\gamma_1^\infty$, is related to $k_H$ by:

$$\gamma_1^\infty = \frac{k_H}{P_1^S}\exp\frac{P_1^S(\overline{V}_1 - B_{11})}{RT}. \quad (3)$$

This relation can be derived from eqs 2, 4 and 5 with the condition of $x_1 \to 0$ and P [in eq 5]→0 for the present solvent (for ionic liquid, P≈0).

$$y_i P \Phi_i = x_i \gamma_i P_i^s, \quad (4)$$

[i=1 for gas (FC-14 or $NF_3$) and i=2 for ionic liquid]
For the present systems, it was assumed that $P_2^s \approx 0$ and $y_2 \approx 0$ (or $y_1 \approx 1$). Thus, eq (4) becomes only one equation with i=1, and the correction factor for non-ideality, $\Phi_1$, can be written as:

$$\Phi_1 = \exp\left[\frac{(B_{11} - \overline{V}_1)(P - P_1^S)}{RT}\right]. \quad (5)$$

The second virial coefficient, $B_{11}(T)$, of pure species 1 can be calculated by proper equation-of-state model (Lemmon, E. W., et al (supra), the saturated molar liquid volume, $\overline{V}_1(T)$, is calculated using the method described in Shiflett, M. B. and Yokozeki, A. (Solubility and Diffusivity of Hydrofluorocarbons in Room-Temperature Ionic Liquids. *AIChE J.* (2006), 52(3), 1205-1219), and R is the universal gas constant. The vapor pressure of pure species 1 is modeled by:

$$\ln P_1^S = A_1 - \frac{B_1}{T + C_1}. \quad (6)$$

The coefficients in eq (6) for FC-14 are ($A_1$=8.1686, $B_1$=1659.12, $C_1$=14.6821) and $NF_3$ are ($A_1$=7.45885, $B_1$=1387.00, $C_1$=−1.7795), and it was assumed that eq (6) holds even above VLE (vapor liquid equilibrium) critical temperature, $T_c$, as an extrapolated hypothetical vapor pressure.

Table 1 provides temperature (T), Henry's constant ($k_H$), the saturated vapor pressure ($P_i^s$), the $2^{nd}$ virial coefficient ($B_{11}(T)$), and the activity coefficient at infinite dilution ($\gamma_1^\infty$).

TABLE 1

| Gas | T (K) | $k_H$ (MPa) | $P_i^S$ (MPa) | $B_{11}$ (cm$^3$ mol$^{-1}$) | $\gamma_1^\infty$ |
|---|---|---|---|---|---|
| $NF_3$ | 287.31 | 149.5 | 13.48 | −96.52 | 19.1 |
| $NF_3$ | 328.20 | 182.1 | 24.77 | −69.34 | 13.8 |
| FC-14 | 298.14 | 740.8 | 17.55 | −91.63 | 80.8 |
| FC-14 | 323.12 | 625.6 | 25.97 | −72.92 | 48.8 |
| FC-14 | 347.99 | 608.0 | 36.38 | −57.22 | 34.3 |

The observed Henry's constants of Table 1 have been well correlated with an empirical form (with errors about 2% of $k_H$):

$$\ln k_H = A + \frac{B}{T}. \quad (7)$$

Using eq (7), the Henry's constants were calculated over a temperature range from 10 C (283.15 K) to 75 C (348.15 K). The infinite dilution activity coefficients were then calculated over the same temperature range using eq (1)-(6) and the results are provided in Table 2.

These activity coefficients at infinite dilution $\gamma_1^\infty$ were used to calculate the selectivity ($\alpha_{ij}$):

$$\alpha_{ij} = \frac{\gamma_i^\infty}{\gamma_j^\infty}$$

where components i and j are present at an infinite degree of dilution in the entrainer and i can represent FC-14, and j can represent $NF_3$. In order to achieve separation, a selectivity of greater than about 1.0 is required. The selectivities ($\alpha_{ij}$) in Table 2 show that the use of [bmim][$PF_6$] as an entrainer will separate FC-14 and $NF_3$ with a selectivity of greater than 3.0 at a temperature of 348.15 K in one case and greater than 5.0 at lower temperatures (i.e. 283.15 K).

TABLE 2

| T (K) | $\gamma_i^\infty$ | $\gamma_j^\infty$ | $\alpha_{ij}$ |
|---|---|---|---|
| 283.15 | 108.4 | 19.7 | 5.5 |
| 298.15 | 80.8 | 17.7 | 4.6 |
| 323.5 | 48.7 | 14.4 | 3.4 |
| 348.15 | 34.3 | 11.2 | 3.1 |

Examples 2-3 provide solubility results for tetrafluoromethane (FC-14) and nitrogen trifluoride ($NF_3$), respectively. These data are used for calculating the Henry's Law Constant ($k_H$) and activity coefficient at infinite dilution ($\gamma_1^\infty$) as shown in Example 1.

EXAMPLE 2

Solubility of Tetrafluoromethane (FC-14) in 1-butyl-3-methylimidazolium Hexafluorophosphate A solubility study was made at temperatures of 24.99, 49.97, and 74.84° C. over a pressure range from 0 to about 1.4 MPa where the solubilities ($x_{meas.}$) were measured using a volumetric view cell.

Tables 3a, 3b and 3c provide data for T, P, f, and $x_{meas}$ at temperatures of 24.99, 49.97 and 74.84° C., respectively.

TABLE 3a

| T (° C.) | P (MPa) | f (MPa) | $x_{meas.}$ (mole %) |
|---|---|---|---|
| 24.99 | 0.1404 | 0.1396 | 0.0197 |
| 24.99 | 0.2773 | 0.2745 | 0.0399 |
| 24.99 | 0.4267 | 0.4200 | 0.0581 |
| 24.99 | 0.6189 | 0.6049 | 0.0874 |
| 24.99 | 0.8207 | 0.7962 | 0.1154 |

TABLE 3b

| T (° C.) | P (MPa) | f (MPa) | $x_{meas.}$ (mole %) |
|---|---|---|---|
| 49.97 | 0.1469 | 0.1463 | 0.0232 |
| 49.97 | 0.2810 | 0.2789 | 0.0446 |
| 49.97 | 0.4143 | 0.4097 | 0.0634 |

TABLE 3b-continued

| T (° C.) | P (MPa) | f (MPa) | $x_{meas.}$ (mole %) |
|---|---|---|---|
| 49.97 | 0.5542 | 0.5460 | 0.0853 |
| 49.97 | 0.6897 | 0.6770 | 0.1036 |
| 49.97 | 0.8315 | 0.8130 | 0.1252 |
| 49.97 | 0.9697 | 0.9446 | 0.1450 |
| 49.97 | 1.1073 | 1.0746 | 0.1633 |
| 49.97 | 1.2452 | 1.2041 | 0.1823 |
| 49.97 | 1.3770 | 1.3268 | 0.1988 |

TABLE 3c

| T (° C.) | P (MPa) | f (MPa) | $x_{meas.}$ (mole %) |
|---|---|---|---|
| 74.84 | 0.1390 | 0.1389 | 0.0235 |
| 74.84 | 0.2820 | 0.2805 | 0.0470 |
| 74.84 | 0.4200 | 0.4166 | 0.0705 |
| 74.84 | 0.5548 | 0.5487 | 0.0909 |
| 74.84 | 0.6921 | 0.6827 | 0.1137 |
| 74.84 | 0.8310 | 0.8176 | 0.1354 |
| 74.84 | 0.9663 | 0.9481 | 0.1570 |
| 74.84 | 1.1073 | 1.0835 | 0.1804 |
| 74.84 | 1.2406 | 1.2109 | 0.2015 |
| 74.84 | 1.3847 | 1.3477 | 0.2235 |

EXAMPLE 3

Solubility of Nitrogen Trifluoride (NF3) in 1-butyl-3-methylimidazolium Hexafluorophosphate A solubility study was made at temperatures of 14.16 and 55.05° C. over a pressure range from 0 to about 1.4 MPa where the solubilities ($x_{meas.}$) were measured using a volumetric view cell.

Tables 4a and 4b provide data for T, P, f and $x_{meas}$ at temperatures of 14.16 and 55.05° C., respectively.

TABLE 4a

| T (° C.) | P (MPa) | f (MPa) | $x_{meas.}$ (mole %) |
|---|---|---|---|
| 14.16 | 0.0609 | 0.0607 | 0.0440 |
| 14.16 | 0.1345 | 0.1337 | 0.0937 |
| 14.16 | 0.2604 | 0.2577 | 0.1752 |
| 14.16 | 0.4049 | 0.3983 | 0.2690 |
| 14.16 | 0.5558 | 0.5434 | 0.3688 |
| 14.16 | 0.6878 | 0.6688 | 0.4477 |
| 14.16 | 0.8305 | 0.8029 | 0.5354 |
| 14.16 | 0.9694 | 0.9320 | 0.6188 |
| 14.16 | 1.0993 | 1.0513 | 0.6961 |
| 14.16 | 1.2413 | 1.1802 | 0.7755 |
| 14.16 | 1.3764 | 1.3014 | 0.8639 |

TABLE 4b

| T (° C.) | P (MPa) | f (MPa) | $x_{meas.}$ (mol. fraction) |
|---|---|---|---|
| 55.05 | 0.1219 | 0.1215 | 0.0562 |
| 55.05 | 0.2629 | 0.2611 | 0.1296 |
| 55.05 | 0.4086 | 0.4044 | 0.2066 |
| 55.05 | 0.5410 | 0.5337 | 0.2771 |
| 55.05 | 0.6822 | 0.6705 | 0.3502 |
| 55.05 | 0.8197 | 0.8028 | 0.4199 |
| 55.05 | 0.9556 | 0.9327 | 0.4849 |

TABLE 4b-continued

| T (° C.) | P (MPa) | f (MPa) | x_meas. (mol. fraction) |
|---|---|---|---|
| 55.05 | 1.0944 | 1.0645 | 0.5536 |
| 55.05 | 1.2363 | 1.1981 | 0.6228 |
| 55.05 | 1.3746 | 1.3275 | 0.6881 |

Certain features of this invention are described herein in the context of an embodiment that combines various such features together, whether as described in the disclosure or in one of the drawings. The scope of the invention is not, however, limited by the description of only certain features within any particular embodiment, and the invention also includes (1) a subcombination of fewer than all of the features of any described embodiment, which subcombination is characterized by the absence of the features omitted to form the subcombination; (2) each of the features, individually, included within the combination of the described embodiment; and (3) other combinations of features formed from one or more or all of the features of the described embodiment together with other features as disclosed elsewhere herein.

In this specification, unless explicitly stated otherwise or indicated to the contrary by the context of usage, where an embodiment of this invention is stated or described as comprising, including, containing, having, being composed of or being constituted by or of certain features or elements, one or more features or elements in addition to those explicitly stated or described may be present in the embodiment. An alternative embodiment of this invention, however, may be stated or described as consisting essentially of certain features or elements, in which embodiment features or elements that would materially alter the principle of operation or the distinguishing characteristics of the embodiment are not present therein. A further alternative embodiment of this invention may be stated or described as consisting of certain features or elements, in which embodiment, or in insubstantial variations thereof, only the features or elements specifically stated or described are present.

In this specification, unless explicitly stated otherwise or indicated to the contrary by the context of usage, use of the indefinite article "a" or "an" with respect to a statement or description of the presence of an element or feature of this invention, does not limit the presence of the element or feature to one in number;

What is claimed is:

1. A process for separating either nitrogen trifluoride or tetrafluoromethane from a mixture that comprises nitrogen trifluoride and tetrafluoromethane, comprising contacting the mixture with at least one ionic liquid, which comprises an organic salt, in which one member of the group of nitrogen trifluoride and tetrafluoromethane is soluble to a different extent than the other member, and separating the lower-solubility member from the mixture; wherein an ionic liquid comprises a fluorinated cation and an $[SbF_6]^-$, anion.

2. The process of claim 1 wherein an ionic liquid comprises a cation selected from the group consisting of the following eleven cations:

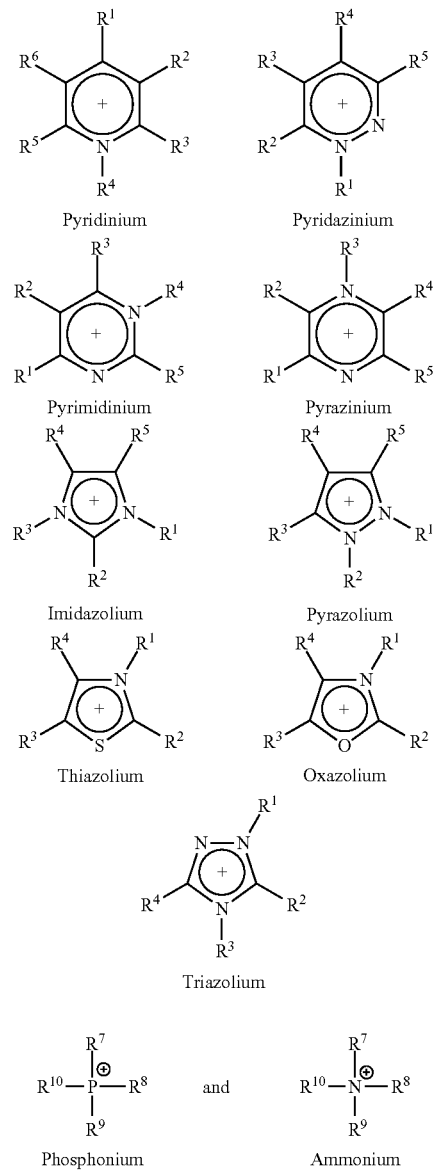

Pyridinium

Pyridazinium

Pyrimidinium

Pyrazinium

Imidazolium

Pyrazolium

Thiazolium

Oxazolium

Triazolium

Phosphonium

Ammonium wherein $R^1$, $R^2$, $R^3$, $R^4$, $R^5$ and $R^6$ are independently selected from the group consisting of:
(i) H
(ii) halogen
(iii) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH;
(iv) —$CH_3$, —$C_2H_5$, or a $C_3$ to $C_{25}$ straight-chain, branched or cyclic alkane or alkene group comprising one to three heteroatoms selected from the group consisting of O, N, Si and S, and optionally substituted with at least one member selected from the group consisting of Cl, Br, F, I, OH, $NH_2$ and SH;
(v) a $C_6$ to $C_{20}$ unsubstituted aryl group, or a $C_3$ to $C_{25}$ unsubstituted heteroaryl group, having one to three heteroatoms independently selected from the group consisting of O, N, Si and S; and
(vi) a $C_6$ to $C_{25}$ substituted aryl group, or a $C_3$ to $C_{25}$ substituted heteroaryl group, having one to three heteroatoms independently selected from the group consisting of O, N, Si and S; and wherein said substituted aryl or substituted heteroaryl group has one to three substituents independently selected from the group consisting of:
(1) —$CH_3$, —$C_2H_5$, or a $C_3$ to $C_{25}$ straight-chain, branched or cyclic alkane or alkene group, optionally substituted with at least one member selected from the group consisting of Cl, Br, F I, OH, $NH_2$ and SH,
(2) OH,
(3) $NH_2$, and
(4) SH;

$R^7$, $R^8$, $R^9$, and $R^{10}$ are independently selected from the group consisting of:
(vii) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH, $NH_2$ and SH;
(viii) —$CH_3$, —$C_2H_5$, or a $C_3$ to $C_{25}$ straight-chain, branched or cyclic alkane or alkene group comprising one to three heteroatoms selected from the group consisting of O, N, Si and S, and optionally substituted with at least one member selected from the group consisting of Cl, Br, F, I, OH, $NH_2$ and SH;
(ix) a $C_6$ to $C_{25}$ unsubstituted aryl group, or a $C_3$ to $C_{25}$ unsubstituted heteroaryl group, having one to three heteroatoms independently selected from the group consisting of O, N, Si and S; and
(x) a $C_6$ to $C_{25}$ substituted aryl group, or a $C_3$ to $C_{25}$ substituted heteroaryl group, having one to three heteroatoms independently selected from the group consisting of O, N, Si and S; and wherein said substituted aryl or substituted heteroaryl group has one to three substituents independently selected from the group consisting of:
(1) —$CH_3$, —$C_2H_5$, or a $C_3$ to $C_{25}$ straight-chain, branched or cyclic alkane or alkene group, optionally substituted with at least one member selected from the group consisting of Cl, Br, F, I, OH $NH_2$ and SH,
(2) OH,
(3) $NH_2$, and
(4) SH; and wherein optionally at least two of $R^1$, $R^2$, $R^3$, $R^4$, $R^5$, $R^6$, $R^7$, $R^8$, $R^9$, and $R^{10}$ can together form a cyclic or bicyclic alkanyl or alkenyl group; wherein said cation is fluorinated.

3. The process of claim 2 wherein at least one of $R^1$, $R^2$, $R^3$, $R^4$, $R^5$, $R^6$, $R^7$, $R^8$, $R^9$, and $R^{10}$ comprises $F^-$.

4. The process of claim 1 which is performed by extractive distillation.

5. The process of claim 1 which is performed by absorption.

6. The process of claim 1 wherein nitrogen trifluoride is recovered as the lower solubility member.

7. The process of claim 6 wherein a nitrogen trifluoride product is recovered that contains less than 10 parts-per-million-molar tetrafluoromethane.

8. The process of claim 1 wherein tetrafluoromethane is recovered as the lower solubility member.

9. The process of claim 8 wherein a tetrafluoromethane product is recovered that contains less than 10 parts-per-million-molar nitrogen trifluoride.

10. The process of claim 1 wherein an ionic liquid is recovered and recycled.

11. A process for separating either nitrogen trifluoride or tetrafluoromethane from a mixture that comprises nitrogen trifluoride, tetrafluoromethane and one or more other compounds as components of the mixture, comprising contacting the mixture with at least one ionic liquid in which one member of the group of nitrogen trifluoride and tetrafluoromethane is soluble to a different extent than either the other member of the group or another component of the mixture, and separating the low solubility member of the group from the mixture; wherein an ionic liquid comprises a fluorinated cation and an $[SbF_6]^-$ anion.

12. The process according to claim 11 wherein other component(s) of the mixture may be selected from one or more compounds or elements in the group consisting of hydrogen fluoride, tetrafluoroethylene methyl fluoride, trifluoromethane chlorotrifluoromethane pentafluoroethane tetrafluoroethane, difluoromethane, hexafluoroethane, octafluorocyclobutane, octafluoropropane, sulfur hexafluoride, nitrogen, oxygen, carbon dioxide, water, methane, ethane, propane and nitrous oxide.

* * * * *